(12) United States Patent
Buding

(10) Patent No.: US 7,217,834 B2
(45) Date of Patent: May 15, 2007

(54) PREPARATION OF THIOSULPHURIC ACID DERIVATIVES

(75) Inventor: Hartmuth Buding, Titz (DE)

(73) Assignee: Lanxess Deutschland GmbH, Leverkusen (DE)

( * ) Notice: Subject to any disclaimer, the term of this patent is extended or adjusted under 35 U.S.C. 154(b) by 85 days.

(21) Appl. No.: 11/105,603

(22) Filed: Apr. 14, 2005

(65) Prior Publication Data

US 2005/0240044 A1   Oct. 27, 2005

(30) Foreign Application Priority Data

Apr. 15, 2004  (DE) .................. 10 2004 018 193

(51) Int. Cl.
*C07C 381/02*  (2006.01)
(52) U.S. Cl. .................................. 560/308
(58) Field of Classification Search ............. 560/308
See application file for complete search history.

(56) References Cited

U.S. PATENT DOCUMENTS 3,869,435 A    3/1975  Trivette, Jr. ............ 260/79.5
4,417,012 A   11/1983  Moniotte ................. 524/83
5,442,099 A    8/1995  Wolpers et al.
5,717,038 A    2/1998  Hörpel et al. ............ 525/332.4

FOREIGN PATENT DOCUMENTS

EP      0 385 072      2/1989

OTHER PUBLICATIONS

Mazover, Y. G. Zhurnal Obshchei Khimii (1949), 19, 843-8. **CAS Abstract attached.*
"Bunte Salts (RSSO$_3$Na)" B. Milligan and J. M. Swan in Rev. Pure and Applied Chemistry 12, 1962, pp. 72-94.
"Zur Chemie der Buntesaize", H. Distler, Angew. Chem. 79, 1967, pp. 520-529.

* cited by examiner

*Primary Examiner*—Kamal A. Saeed
*Assistant Examiner*—Jason M. Nolan
(74) *Attorney, Agent, or Firm*—Michael A. Miller

(57) ABSTRACT

The invention relates to a novel process for preparing salts of S-alkyl esters of thiosulphuric acid by reacting organic dihalides with thiosulphates in water.

7 Claims, No Drawings

PREPARATION OF THIOSULPHURIC ACID DERIVATIVES

The invention relates to a process for preparing salts of S-alkyl esters of thiosulphuric acid.

The preparation of salts of S-alkyl esters of thiosulphuric acid (Bunte salts) is known in principle (cf., for example, B. Milligan and J. M. Swan in Rev. Pure and Applied Chemistry 12, 1962, pages 72 to 94, and H. Distler in Angew. Chem. 79, 1967, pages 520 to 529).

According to B. Milligan et al., Bunte salts are generally prepared by reacting alkyl halides with sodium thiosulphate in a boiling solution of 50% aqueous ethanol (page 74, right-hand column, 3rd paragraph). Only in the case of water-soluble alkyl halides is water used as the sole solvent.

EP-A 70 143 describes a 1:1 mixture of water and ethanol as the solvent for preparing the sodium salt hydrate of hexamethylene 1,6-bisthiosulphate. However, the inventive solvents disclosed are ethylene glycol and diethylene glycol (page 16, lines 2 to 9). Any water present in the ethylene glycol or diethylene glycol, and also water of crystallization in the thiosulphate, is removed by distillation before the dihalide is added. The reaction products dissolved in the glycolic solvents are precipitated by adding certain solvents. One such solvent (precipitant) which is mentioned is isopropanol. A disadvantage of this process is firstly that the glycols and the thiosulphate have to be dewatered by distillation before the start of the reaction, and secondly that large amounts of organic solvents (glycols and precipitant) have to be handled. At the end of the synthesis, the glycols and the precipitant have to be worked up by distillation, which is costly and inconvenient.

DE-A 22 56 511 describes, inter alia, on page 40 the preparation of a bis-Bunte salt as follows: 1,4-dichlorobutene-2 is reacted in aqueous ethanol with sodium thiosulphate pentahydrate at the boiling temperature of the solvent mixture and then the ethanol is removed by distillation on completion of reaction. The bis-Bunte salt dissolved in water is then used without isolation as a reactant for a further synthetic stage. A disadvantage of this process is the necessary distillative removal of the ethanol from the reaction mixture.

A reworking of the teaching of DE-A 22 56 511 using the example of 1,6-dichlorohexane had the following result: when ethanol was distilled out of the reaction mixture of the reaction of 1,6-dichlorohexane with sodium thiosulphate pentahydrate in a mixture of ethanol and water, it was observed that the ethanol entrains malodorous by-products from the reaction mixture and thus makes the distillate unusable without additional, costly and inconvenient purification thereof, so that it has to be sent to an incineration. In addition, the distillation column was soiled by greasy deposits of the malodorous by-products in some cases when the ethanol was distilled off, which necessitated column cleaning.

The patent applications EP-A 385 072 and EP-A 432 417 detailed the synthesis of bis-Bunte salts in a very general manner using the example of the reaction of 1,2-dichloroethane with sodium thiosulphate in aqueous solution. No statements are made about reaction parameters to be employed advantageously. Nor are any working examples for the synthesis given. In-house experiments on the reworking of the general information of EP-A 432 417 using the example of 1,6-dichlorohexane gave rise to a conversion of the dihalide used of only approx. 89% (cf. Example 6). Such low conversions of the dihalide necessitate a distillative removal thereof from the reaction mixture, followed by a workup for the purpose of recycling. In addition, it is suspected that such low conversions of the α,ω-dihaloalkane, in spite of excess of sodium thiosulphate, give rise not only to the desired bis-Bunte salt but also to a considerable extent to the undesired product in which only one halogen atom has been replaced by the S—SO$_3$Na group.

It is an object of the present invention to provide a simple, industrially readily practicable, environmentally friendly and non-resource-intensive process for preparing salts of S-alkyl esters of thiosulphuric acid in water, without addition of alcohols and/or glycols, with high conversions of the parent α,ω-dihaloalkanes and with industrially good yields and high contents of the salts of the S-alkyl esters of thiosulphuric acid.

It is not possible to achieve the aim set by the known preparation processes.

It has now been found that virtually water-insoluble α,ω-dihaloalkanes can be reacted in water as a reaction medium in the absence of alcohols and/or glycols with thiosulphate ions while maintaining a certain pH range in high conversions to give bis-Bunte salts with industrially good yields and high contents.

The present invention therefore provides a process for preparing the compounds of the formula (I)

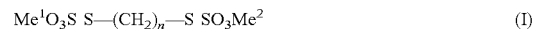

$$\text{Me}^1\text{O}_3\text{S—S—(CH}_2)_n\text{—S SO}_3\text{Me}^2 \qquad (I)$$

where Me$^1$ and Me$^2$ are the same or different and are each monovalent metal ions or ammonium ions and n is an integer from 2 to 8, characterized in that compounds of the formula (II)

$$\text{X—(CH}_2)_n\text{—X} \qquad (II),$$

where X is halogen and n is as defined in formula (I)

are reacted with thiosulphate ions at a reaction temperature of 80° to 150° C., the reaction being carried out in water without addition of alcohols and/or glycols in a pH range of 3 to 9.8.

The serial number n in the formula (I) is an integer from 2 to 8, preferably from 3 to 8, most preferably from 4 to 8.

In the formula (I), Me$^1$ and Me$^2$ are the same or different and are each monovalent metal ions or ammonium ions. Me$^1$ and Me$^2$ are preferably the same and are each alkali metal or ammonium ions, preferably alkali metal ions. Of the alkali metal ions, preference is given to sodium and potassium ions, very particular preference to sodium ions.

In the formula (II), X is preferably chlorine or bromine. The inventive compounds of the formula (II) may also be mixed halides, i.e. may simultaneously contain different halogen atoms.

The reaction of the compounds of the formula (II) is carried out in a closed or open system with thiosulphate ions without addition of alcohols and/or glycols in water. The thiosulphate ions are preferably used in the form of alkali metal thiosulphates or in the form of ammonium thiosulphate. From the group of the alkali metal thiosulphates, preference is given to the use of sodium thiosulphate or sodium thiosulphate pentahydrate for reasons of availability; however, it is also possible in principle to use lithium thiosulphate, potassium thiosulphate, caesium thiosulphate or rubidium thiosulphate, or mixtures thereof.

When the inventive reaction mixture does not have a pH in the range from 3 to 9.8 at room temperature directly before the start of the reaction, it is advantageous to appropriately set a pH in this range by adding acids or bases, preferably with mineral acids, for example hydrochloric acid, or by solutions of alkali metal hydroxides, for example sodium hydroxide, in order then to start the inventive reaction afterwards.

The pH of the reaction mixture is kept or set during the reaction in the context of the invention within the range from 3 to 9.8, preferably from 4 to 9.4, most preferably from 5 to 9.

It has been found that the reaction mixture becomes ever more acidic as the reaction progresses in the reaction of the compounds of the formula (II) with thiosulphate ions.

In that case, the pH is adjusted during the inventive reaction of the compounds of the formula (II) by adding organic or inorganic bases or mixtures thereof. Useful organic bases for the invention are preferably tertiary alkylamines having a hydrocarbon radical of 2 to 14 carbon atoms. Useful inorganic bases for the invention are preferably alkali metal or alkaline earth metal hydroxides, most preferably alkali metal hydroxides. From the group of the alkali metal hydroxides, preference is given to sodium hydroxide or potassium hydroxide, very particular preference to sodium hydroxide. Of the bases for establishing the inventive pH range, preference is given to the inorganic bases. However, the inventive pH values may also be established by a buffer system which does not have a negative influence on the inventive reaction and has good wastewater compatibility, for example sodium hydrogencarbonate. The optimum dosage may be determined readily by experiments.

To adjust the pH in the inventive reaction of the compounds of the formula (II) with thiosulphate ions, the base may be added as such or else as an aqueous solution. Preference is given to adding the base to the reaction mixture as a very dilute aqueous solution in order to achieve rapid distribution and thus rapid pH adjustment. In the case of sodium hydroxide and potassium hydroxide, a 0.01 to 15% by weight, preferably 0.1 to 10% by weight, aqueous solution is particularly suitable. For other bases, the optimal concentration can be determined readily by experiments.

The inventive amount of thiosulphate to be used is approx. 200 to 250 mol %, preferably 200 to 240 mol %, most preferably 200 to 230 mol %, based on the moles of compounds of the formula (II) used. Although it is possible to use smaller amounts of thiosulphate, they are at the expense of the yield and the contents of bis-Bunte salt. Larger amounts of thiosulphate may likewise be used, but they are undesired not only from an ecological point of view with regard to the wastewater, but also with regard to by-products which form.

The amount of water to be used as the reaction medium in the inventive reaction of the compounds of the formula (II) with thiosulphate is not critical. Against the background of minimum amounts of wastewater in the isolation of the compounds of the formula (I) or in a subsequent reaction stage without isolation of the compounds of the formula (I), the minimum amount of water should be selected in the reaction of the compounds of the formula (II). However, the amount of water selected should advantageously be sufficiently large that the thiosulphate used and also the compounds of the formula (I) which form are still just dissolved at reaction temperature in the reaction mixture.

The inventive reaction temperatures for the preparation process according to the invention are approx. 80° to 150° C., preferably 85° to 140° C., most preferably 90° to 130° C. In the open system at standard pressure, the boiling temperature of the reaction mixture is advantageously used. The conversion for the compounds of the formula (II) in the reaction with thiosulphate ions in the context of the invention is at least 94%, preferably at least 96%, most preferably at least 98%. The conversion of the compounds of the formula (II) can be determined, for example, by means of gas chromatography (internal or external standard) in the reaction mixture. The pure yield (=purity×content) of the salts of the S-alkyl esters of thiosulphuric acid is at least 70%, preferably at least 75%, most preferably at least 80%, after the preparation process according to the invention.

Since the compounds of the formula (II) are virtually insoluble in water, good mixing of the reaction mixture, for example by stirring, has to be ensured in the course of the inventive conversion thereof.

The inventive compounds of the formula (I) may be used, for example, in the form of their aqueous reaction mixture on completion of conversion of the compounds of the formula (II) as building blocks for chemical syntheses. In isolated form, the inventive compounds of the formula (I), optionally containing water of crystallization, may be used, for example, to crosslink diene rubbers in combination with sulphur and accelerants.

If required, the inventive compounds of the formula (I) may be reacted with metal cations with exchange of the inventive cations $Me^1$ and $Me^2$. This may be effected, for example, in aqueous solution with the aid of cation exchange resins correspondingly laden with metal cations.

EXAMPLES

Example 1

A nitrogen-purged 21 four-necked stirred flask apparatus with internal thermometer, reflux condenser with bubble counter and pH electrode was initially charged with stirring with 300 g of demineralized water and 136.5 g (0.55 mol) of sodium thiosulphate pentahydrate. After the thiosulphate had dissolved, 38.8 g (0.25 mol) of 1,6-dichlorohexane were added. The weakly acidic mixture was adjusted to pH 7.2 with a few drops of 2.5% sodium hydroxide solution. The reaction vessel was flushed once more briefly with nitrogen and the mixture was then boiled at reflux for 9 h, and the pH of the reaction mixture was kept during this time at 7.2±0.1 (pH electrode) by adding 2.5% sodium hydroxide solution by means of a metering pump. After in each case 6 and 8 hours of the reaction, the bubble counter was briefly removed from the reflux condenser. In each case approx. 5 ml of demineralized water were sprayed with a wash bottle into the reflux condenser from the top in order to flush back any 1,6-dichlorohexane which has not dripped back into the flask. After the reaction time had ended, approx. 15 ml of 2.5% sodium hydroxide solution were consumed in the pH control. The reaction mixture was clear and homogeneous. After brief cooling, a sample was taken from the reaction mixture to determine the conversion of 1,6-dichlorohexane by gas chromatography (GC). The GC analysis with internal standard give a residual content of 1,6-dichlorohexane of <10 ppm, which corresponds to a conversion of 1,6-dichlorohexane of >99.9%.

Somewhat flocculent precipitate of the disodium salt dihydrate of hexamethylene 1,6-bisthiosulphate crystallized overnight out of the reaction mixture containing sodium thiosulphate and a large amount of sodium chloride. This precipitate was isolated by means of a sintered glass frit, washed twice with approx. 25 ml of ethanol each time and dried at 50° C. in a vacuum drying cabinet. Approx. 3.7 g of fine crystal powder were obtained which, according to elemental analysis, based on the disodium salt dihydrate of hexamethylene 1,6-bisthiosulphate, was not quite analytically pure:

| | | |
|---|---|---|
| C calc.: 18.46% | H calc.: 4.13% | S calc.: 32.85% |
| C found: 17.3/17.3% | H found: 3.5/3.5% | S found: 32.0/32.9% |

The IR spectrum (KBr) of this crude crystal powder was in agreement with the expected structure:

| | |
|---|---|
| 3564, 3458 cm$^{-1}$ | (water of crystallization) |
| 2927, 2858 cm$^{-1}$ | (CH valence) |
| 1619 cm$^{-1}$ | (OH deformation) |
| 1465 cm$^{-1}$ | (CH$_2$, asymmetric deformation) |
| 1214, 1048, 654 cm$^{-1}$ | (S—SO$_3^{-1}$) |

Concentration of the mother liquor allows further products to be obtained.

To determine the yield, the reaction was repeated once again. However, a GC analysis sample was not taken from the reaction mixture. The pure yield of the disodium salt dihydrate of hexamethylene 1,6-bisthiosulphate was approx. 93.3%[1] in this reaction.

[1] The pure yield of the disodium salt dihydrate of hexamethylene 1,6-bisthiosulphate was determined indirectly from the yield of a subsequent reaction of the resulting reaction solution as follows: reaction of the inventive reaction solution with an aqueous sodium dibenzyldithiocarbamate solution (NaBEC solution) provided, after workup, approx. 156.9 g of crystals (90.5% of theory). The content of 1,6-bis(N,N-dibenzylthiocarbamoyldithio) hexane was determined by means of HPLC (external standard) to be approx. 96%. This gives a pure yield of 1,6-bis(N,N-dibenzylthio-carbamoyldithio)hexane of approx. 86.9%. Reaction of the disodium salt dihydrate of hexamethylene 1,6-bisthiosulphate having a content of 98% (Duralink® HTS from Flexsys/Belgium) in aqueous solution with NaBEC solution under the same reaction conditions as in the reaction outlined above provided 1,6-bis(N,N-dibenzylthio-carbamoyldithio)hexane in a yield of 96% (of theory) and with a content of approx. 99%, which corresponds to a pure yield of 96%×0.99×0.98=93.1%. Therefore, the pure yield of the disodium salt dihydrate of hexamethylene 1,6-bisthiosulphate in the inventive reaction of 1,6-dichlorohexane with sodium thiosulphate pentahydrate must have been approx. 93.3% (86.9×1/0.931=93.3%).

Examples 2 to 5

The procedure of Example 1 was repeated, except that the reaction of 1,6-dichlorohexane was carried out at a constant pH of 5, 6, 8 and 9. Before the start of the particular reaction, the weakly acidic mixture was adjusted to the pH of 5, 6, 8 and 9 with 2.5% sodium hydroxide solution (measurement with pH electrodes).

| | Example 2 | Example 3 | Example 4 | Example 5 |
|---|---|---|---|---|
| pH value in the reaction | 5.0 ± 0.1 | 6.0 ± 0.1 | 8.0 ± 0.1 | 9.0 ± 0.1 |
| Residual 1,6-dichlorohexane content (ppm) | <10 | <10 | <10 | approx. 11 |
| Conversion of 1,6-dichlorohexane (%) | >99.9 | >99.9 | >99.9 | >99.9 |

In all examples (Examples 2 to 5), the resulting reaction mixture was clear and homogeneous.

To determine the pure yield with respect to Examples 2 and 5, they were repeated once more. However, a GC analysis sample was not taken from the particular reaction mixture. The pure yield of the (di)sodium salt (di)hydrate of hexamethylene 1,6-bisthiosulphate was approx. 91.4%[2] for the repetition of Example 2 and approx. 90.6%[2] for the repetition of Example 5.

[2] The pure yield for the synthesis according to Examples 2 and 5 was carried out again as in Example 1 by reacting the reaction solutions obtained in each case with aqueous NaBEC solution. In this procedure, the yield of 1,6-bis(N,N-dibenzylthiocarbamoyldithio)hexane was approx. 89.6% of theory with a content of 95% for the reaction according to Example 2 and approx. 89.7% of theory with a content of approx. 94% for that according to Example 5. Thus, the pure yield of the (di)sodium salt (di)hydrate of hexamethylene 1,6-bisthiosulphate in the inventive reaction of 1,6-dichlorohexane with sodium thiosulphate pentahydrate must have been approx. 91.4% for the reaction according to Example 2 (89.6%×0.95×1/0.931=91.4%) and approx. 90.6% for that according to Example 5 (89.7%×0.94×1/0.931=90.6%).

Example 6

Comparative Example Analogous to EP-A 432 417, Page 4, Lines 50 to 54

The procedure of Example 1 was repeated. However, a pH adjustment or a pH correction was carried out neither before nor during the reaction of 1,6-dichlorohexane. The pH migrated from the range of approx. 6 to 7 at the start of the reaction at boiling to approx. 2.7 at the end of the reaction time. For the GC analysis, a sample was taken from the yellowish reaction mixture of slightly opaque appearance. In this sample, a residual content of 1,6-dichlorohexane of approx. 0.9% (9000 ppm) was determined, which corresponds to a conversion of only approx. 89%.

To determine the yield, the experiment was repeated without sampling for a GC analysis. At the end of this repeat experiment, the pH at boiling was approx. 1.8. Unconverted 1,6-dichlorohexane was distilled azeotropically out of the reaction mixture at standard pressure together with water. The total mass of dihalides and water which has been distilled off of approx. 120 g was added again to the mixture in the form of demineralized water. The pure yield of the (di)sodium salt (di)hydrate of hexamethylene 1,6-bisthiosulphate was approx. 16.4%[3].

[3] The pure yield determination was again carried out as in Example 1 by reacting the resulting reaction solution with aqueous NaBEC solution. Approx. 44.8 g (25.8% of theory) of tacky solid having a content of 1,6-bis(N,N-dibenzylthiocarbamoyldithio)hexane of approx. 52% were obtained. Oily yellow material which separated in the mother liquor in the course of suction filtration was removed by extraction with toluene. After toluene had been evaporated off, approx. 19.1 g (11.0% of theory) of viscous, yellow oil was obtained which, according to HPLC, had a content of approx. 17% of 1,6-bis(N,N-dibenzylthiocarbamoyldithio)hexane. This gives a total pure yield of 1,6-bis(N,N-dibenzylthiocarbamoyldithio) hexane of approx. 15.3%. Thus, the pure yield of the (di)sodium salt (di)hydrate of hexamethylene 1,6-bisthiosulphate in the reaction of 1,6-dichlorohexane with sodium thiosulphate pentahydrate according to the prior art must have been approx. 16.4% (15.3%×1/0.931=16.4%).

Evaluation: According to this prior art, the (di)sodium salt (di)hydrate of hexamethylene 1,6-bisthiosulphate is obtained in a completely unsatisfactory pure yield.

Example 7

Comparative Example at pH 10

The procedure of Example 1 was repeated, except that the reaction of 1,6-dichlorohexane was carried out from start to finish at a pH of 10.0±0.1. Before the start of the reaction, the weakly acidic mixture was adjusted to pH 10 with a few drops of 2.5% sodium hydroxide solution. At the end of the reaction time, approx. 135 ml of 2.5% sodium hydroxide solution had been consumed. The finished reaction mixture at boiling exhibited some white precipitate. The GC analysis on the finished reaction mixture gave a residual content of 1,6-dichlorohexane of approx. 23 ppm which corresponds to a conversion of >99.9%.

The reaction was repeated once again, but without taking a GC analysis sample. The pure yield of the (di)sodium salt (di)hydrate of hexamethylene 1,6-bisthiosulphate was approx. 63.1%[4].

[4] The pure yield determined was again carried out as in Example 1 by reacting the resulting reaction solution with aqueous NaBEC solution. A very fine precipitate was obtained whose isolation from the reaction mixture by means of a suction filter took several hours. For this reason, the solid from the suction filter was not washed. Instead of this, the filtercake was removed, slurried with saturated sodium chloride solution and then extracted with toluene. The aqueous phase was extracted once again with toluene. The combined toluenic phases were washed first with saturated sodium chloride solution and then with demineralized water. After the toluene had been evaporated on a rotary evaporator under reduced pressure and subsequently dried in a vacuum drying cabinet at 50° C. to constant weight, approx. 114.3 g (66.0% of theory) of viscous oil were obtained and crystallized after a prolonged period. The content of 1,6-bis(N,N-dibenzythiocarbamoyldithio)hexane was approx. 89%. Therefore, the pure yield of the (di)sodium salt (di)hydrate of hexamethylene 1,6-bisthiosulphate in the reaction of 1,6-dichlorohexane with sodium thiosulphate pentahydrate must have been approx. 63.1% (66.0%×0.89×1/0.931=63.1%).

Evaluation: Above the inventive pH range, the (di)sodium salt (di)hydrate of hexamethylene 1,6-bisthiosulphate was obtained in only insufficient pure yield.

The invention claimed is:

1. Process for preparing the compounds of the formula (I)

$$Me^1O_3S\ S\text{—}(CH_2)_n\text{—}S\ SO_3Me^2 \qquad (I)$$

where $Me^1$ and $Me^2$ are the same or different and are each monovalent metal ions or ammonium ions and n is an integer from 2 to 8, characterized in that compounds of the formula (II)

$$X\text{—}(CH_2)_n\text{—}X \qquad (II)$$

where X is halogen and n is as defined in formula (I) are reacted with thiosulphate ions at a reaction temperature of 80° to 150° C., the reaction being carried out in water without addition of alcohols and/or glycols in a pH range of 3 to 9.8.

2. Process according to claim 1, characterized in that the reaction is carried out in a pH range of 4 to 9.4.

3. Process according to claim 1, characterized in that the reaction is carried out at temperatures of 85° C. to 140° C.

4. Process according to claim 1, characterized in that 200 to 250 mol % of thiosulphate is used based on moles of organic dihalogen compounds of the formula (II) used.

5. The process according to claim 1, wherein the reaction is carried out at a pH ranging from 5 to 9.

6. The process according to claim 1, wherein the serial number n in formula (I) comprises an integer ranging from 4 to 8.

7. A process for preparing the compounds of the formula (I)

$$Me^1O_3S\ S\text{—}(CH_2)_n\text{—}S\ SO_3\ Me^2 \qquad (I)$$

where $Me^1$ and $Me^2$ are the same or different and are each monovalent metal ions or ammonium ions and n is an integer from 4 to 8, characterized in that compounds of the formula (II)

$$X\text{—}(CH_2)_n\text{—}X \qquad (II)$$

where X is halogen and n is as defined in formula (I) are reacted with thiosuiphate ions at a reaction temperature of 80° to 150° C., the reaction being carried out in water without addition of alcohols and/or glycols in a pH range of 5 to 9.

* * * * *